United States Patent
Ito et al.

(10) Patent No.: US 6,692,758 B1
(45) Date of Patent: Feb. 17, 2004

(54) INSERTION STABILIZERS FOR IMPLANTS

(75) Inventors: Masatoshi Ito, Yokohama (JP); Yuriko Kawai, Kamakura (JP); Seiji Okazaki, Kamakura (JP); Masahiko Tanahashi, Kamakura (JP); Kang Jung Kim, Tokyo (JP); Miho Iwase, Chigasaki (JP)

(73) Assignee: Toray Industries, Inc., Tokyo (JP)

( * ) Notice: Subject to any disclaimer, the term of this patent is extended or adjusted under 35 U.S.C. 154(b) by 195 days.

(21) Appl. No.: 09/806,151

(22) PCT Filed: Jul. 26, 2000

(86) PCT No.: PCT/JP00/04794

§ 371 (c)(1),
(2), (4) Date: Mar. 28, 2001

(87) PCT Pub. No.: WO01/08690

PCT Pub. Date: Feb. 8, 2001

(30) Foreign Application Priority Data

Aug. 2, 1999 (JP) .............................. 99/218464

(51) Int. Cl.⁷ ............................................ A61K 31/663
(52) U.S. Cl. ...................................... 424/422; 424/423
(58) Field of Search ................................ 424/422, 423

(56) References Cited

FOREIGN PATENT DOCUMENTS

| EP | 0 594 857 | * | 5/1994 |
| WO | WO 95/30421 | * | 11/1995 |
| WO | WO 96/39107 | * | 12/1996 |

OTHER PUBLICATIONS

Aiman Etiology and treatment of fibrous dysplasia Current Opinion in Orthopaedics pp. 25–29 1997.*

Weinstein Long–term aminobisphosphonate treatment of fibrous dysplasia: spectacular increase in bone density J. Bone and Mineral Res. 12(8):1314–5 1997.*

Chapurlat et al Long–term effects of intravenous pamidronate in fibrous dysplasia of bone J. Bone and Mineral Res. 12(10):1746–1752 1997.*

Rupp, E. et al. Wpecific bioactivites of monocyte–derived interleukin 1 alpha and interleukin 1 beta are simiular to each other on cultured murine thymocytes and on cultured human connective tissue cells J. Clin. Invest. 78(3):836–839.*

Bunning, R. et al. Homogeneous interferon–beta–inducing 22K factor (IL–1 beta) has conncetive tissue cell stimulating activities Biochemical and Biophysical Research Communications 139(3):1150–1157 1986.*

Monkkonen, Jukka et al.: "Effects of tiludronate and ibandronate on the secretion of proinflammatory cytokines and nitric oxide from macrophages in vitro.", Life Sci., 1998, vol. 62, No. 8, pp. PL95–PL102.

Haynes, D. R. et al.: "Potential pharmacological treatments of prosthetic joint loosening.", Inflammopharmacology, 1995, vol. 3, No. 3, pp. 213–219.

Dunn. Colin J. et al.: "Demonstration of novel antiarthritic and antiinflammatory effects of diphonates.", J. Pharmacol. Exp. Ther., 1993.

* cited by examiner

*Primary Examiner*—Thurman K. Page
*Assistant Examiner*—Rachel M. Bennett
(74) *Attorney, Agent, or Firm*—Nixon & Vanderhye P.C.

(57) ABSTRACT

The present invention relates to an implant attachment stabilizer having, as an effective component, a methanebisphosphonic acid derivative represented by general formula (I)

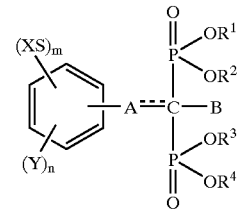

[where, in the formula, X, Y, m, n, ===, A, B, $R^1$, $R^2$, $R^3$ and $R^4$ are as defined in the Specification], or hydrate thereof.

The methanebisphosphonic acid derivatives represented by general formula (I) or the hydrates thereof, to which the present invention relates, have an interstitial tissue proliferation inhibiting action and an osteolytic factor production inhibiting action and, in particular, since they inhibit osteolysis through the inhibition of the interstitial tissue proliferation which accompanies implant attachment and the inhibition of osteolysis factor production at the implant periphery, they are effective in the prevention of implant loosening and detachment, and it is possible to extend the implant attachment period in the case of implants such as artificial joints, and implants in the oro-dental field.

6 Claims, No Drawings

INSERTION STABILIZERS FOR IMPLANTS

This application is a 371 of PCT/JP00/04974 filed Jul. 26, 2000.

The present invention relates to an implant attachment stabilizer, an interstitial tissue proliferation inhibitor and an osteolytic factor production inhibitor having, as an effective component, a methane-bisphosphonic acid derivative or hydrate thereof.

TECHNICAL BACKGROUND

In osteolysis or bone destruction occurring in acute or chronic inflammation involving bone, not only bone resorption by osteoclasts but also interstitial tissue proliferation or produced osteolytic factors are involved to a considerable extent, but no basic medication therefor has been discovered. Furthermore, in the case of the attachment of the implants such as artificial joints carried out in the orthopaedic surgery and dentistry fields, a problem which arises is that, following attachment, loosening occurs and detachment finally results. Consequently, the implant must be reattached by another surgical operation and this imposes an interim lowering in quality of life and a financial burden on the patient. The cause of implant loosening and detachment is considered to be the occurrence of damage to tissues such as bone present at the implant periphery. In particular, in bone tissue, bone resorption markedly increases and osteolysis occurs.

At present, in order to inhibit such bone resorption at the time of implant attachment, consideration is being given to the use of the oestrogen agents [*J. Clin. Invest.*, 89 (1), 74–78 (1992)] and bisphosphonic acids employed as osteoporosis remedies in humans. In fact, a method for treating/preventing prosthesis peripheral bone loss using bisphosphonate bone resorption inhibitors such as Alendronate [(4-amino-1-hydroxybutylidene)-1,1-bisphosphonic acid], which is a bisphosphonic acid compound, has been disclosed [U.S. Pat. No. 5,646,134]. Furthermore, in the case of 1-hydroxyethane-1,1-bisphosphonic acid, there is a report that this inhibits the bone resorption occurring as a result of artificial joint wear debris produced at the time of artificial joint use [*Acta Orthopaedica Scandinavica*, 67 (3), 221–228 (1996)]. However, on the other hand there is also a report suggesting that 1-hydroxyethane-1,1-bisphosphonic acid inhibits the expression and activity of osteoblasts, which play a role in forming bone, so that difficulties arise in its use at the time of implant attachment [*Acta Histochemica*, 96 (2), 181–195 (1994)]. Furthermore, regarding Alendronate too, there is a report that it cannot prevent artificial joint loosening [*Acta Orthopaedica Scandinavica*, 70 (1), 67–70 (1999)] and it is unlikely that the manifestation of an adequate effect can be expected.

Furthermore, the use of the aforementioned compounds is in each case based on the fact that they have a direct inhibitory action on the osteoclasts which play a role in resorbing and breaking-down bone, and no mention is made of the effects on the proliferation of interstitial tissue such as granulation tissue and the production of the osteolytic factors produced by interstitial tissue, which occur prior to the bone tissue destruction. As known examples of osteolytic factors, there are interleukin-1, TNFα and other such cytokines. For example, early in the 1980s it was proved using an organ culture of bone that interleukin-1 has a powerful osteolytic action [*Nature*, 306, 378–380 (1983)]. Furthermore, in a rat foetal bone organ culture system, it has been reported that TNFα acts in osteolysis [*Nature*, 319, 516 (1986)] and that it acts synergistically with interleukin-1. There is also a report that Alendronate [(4-amino-1-hydroxybutylidene)-1,1-bisphosphonic acid] inhibits the production of interleukin-1, interleukin-6 and TNFα from activated macrophage (*Journal of Bone and Mineral Research*, 11, 1719–1725 (1995)), but it is reported that it cannot prevent artificial joint loosening (*Acta Orthopaedica Scandinavica*, 70 (1), 67–70 (1999)). Thus, it is clear that the prevention of implant loosening is not simply linked to an inhibition of cytokine production. Furthermore, it has been reported that bisphosphonic acids such as Clodronate (dichloromethanebisphosphonic acid) inhibit the proliferation of granulation tissue around the antigen in delayed hypersensitivity, which is an allergic reaction condition (*Journal of Pharmacology and Experimental Therapeutics*, 266, 1691–1698 (1993)), but the non-allergic proliferation of granulation tissue formed as a result of implant attachment is not mentioned at all. Consequently, there are no disclosed examples of the use, as implant stabilizers, of drugs which inhibit the aforementioned interstitial tissue proliferation and production of osteolytic factors such as interleukin-1 and TNFα, which occur prior to bone resorption at the periphery of implants and cause implant loosening and detachment. On the other hand, in JP-B-8-26048, there are disclosed methanebisphosphonic acid derivatives having an anti-inflammatory effect, an antirheumatic effect, a metabolic bone disorder improving effect, an interleukin-1 inhibiting effect and an antioxidation effect, but there is no disclosure at all relating to implant attachment stabilization efficacy.

An objective of the present invention lies in offering a novel implant attachment stabilizer for preventing the loosening and detachment of, for example, artificial joints and dental implants, and for extending the implant attachment period. Other objectives of the invention lie in offering an interstitial tissue proliferation inhibitor and an osteolytic factor production inhibitor.

DISCLOSURE OF THE INVENTION

As a result of painstaking study based on the aforesaid objectives, the present inventors have discovered that methanebisphosphonic acid derivatives represented by general formula (I), or hydrates thereof, inhibit interstitial tissue proliferation and inhibit osteolytic factor production, and, furthermore, they have discovered that by means of this inhibition of the proliferation of interstitial tissue accompanying implant attachment and the inhibition of the production of osteolytic factors such as interleukin-1 and TNFα at the implant periphery, the implant attachment period may be extended, and it is on these discoveries that the present invention is based.

In order to realise the aforementioned objectives, the present invention has the following constitution. Specifically, the present invention offers an implant attachment stabilizer, an interstitial tissue proliferation inhibitor and an osteolytic factor production inhibitor having, as an effective component, a methanebisphosphonic acid derivative represented by general formula (I)

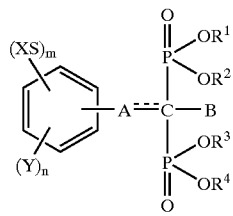

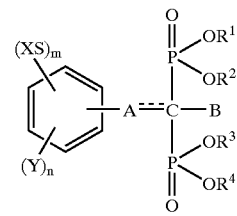

[where, in the formula, X represents a straight chain or branched chain unsubstituted, or nitrogen, oxygen or silicon atom substituent-containing, alkyl group with from 1 to 8 carbon atoms, a phenyl group or a naphthyl group (the phenyl or naphthyl group may also be substituted with a straight chain or branched chain alkyl group having from 1 to 8 carbon atoms, a straight chain or branched chain alkoxy group having from 1 to 8 carbon atoms, a halogen or a hydroxyl group), Y represents a straight chain or branched chain alkyl group having from 1 to 8 carbon atoms, a trifluoromethyl group, a straight chain or branched chain alkenyl group having from 2 to 8 carbon atoms, a cycloalkyl group having from 3 to 8 carbon atoms, an alkoxy group having from 1 to 8 carbon atoms or a halogen (excepting para-substituted chlorine), m and n represent 0, 1, 2 or 3, === represents a double bond or a single bond, A is —$(D)_b$—$(CH_2)_c$— (where D is sulphur, oxygen or $NR^5$ (where $R^5$ represents hydrogen or a straight chain or branched chain alkyl group having from 1 to 8 carbon atoms), or $CH_2$, b is 0 or 1, c is 0, 1, 2, or 3), or —$(CH=CH)_d$—CH= (where d is 0 or 1, and when A represents —$(CH=CH)_d$—CH=, B is not present), B represents hydrogen, a straight chain or branched chain alkyl group having from 1 to 8 carbon atoms, a hydroxyl group or a trialkylsiloxy group (where the alkyl groups are straight chain or branched chain alkyls having from 1 to 8 carbon atoms), and $R^1$, $R^2$, $R^3$ and $R^4$ are each hydrogen, a straight chain or branched chain alkyl group having from 1 to 8 carbon atoms or a pharmacologically permitted cation, and they may be the same or different], or a hydrate thereof.

Furthermore, the present invention is an implant attachment stabilization method, a method for inhibiting interstitial tissue proliferation and a method for inhibiting osteolytic factor production, characterized in that there is administered an effective dose of an aforesaid methanebisphosphonic acid derivative represented by general formula (I) or hydrate thereof.

Again, the present invention comprises the use of an aforesaid methanebisphosphonic acid derivative represented by general formula (I), or hydrate thereof, in order to produce an implant attachment stabilizer, an interstitial tissue proliferation inhibitor and an osteolytic factor production inhibitor.

OPTIMUM FORM FOR PRACTISING THE INVENTION

The present invention is an implant attachment stabilizer, an interstitial tissue proliferation inhibitor and a osteolytic factor production inhibitor having as an effective component a methanebisphosphonic acid derivative represented by the general formula (I)

[where, in the formula, X represents a straight chain or branched chain unsubstituted, or nitrogen, oxygen or silicon atom substituent-containing, alkyl group with from 1 to 8 carbon atoms, a phenyl group or a naphthyl group (the phenyl or naphthyl group may also be substituted with a straight chain or branched chain alkyl group having from 1 to 8 carbon atoms, a straight chain or branched chain alkoxy group having from 1 to 8 carbon atoms, a halogen or a hydroxyl group), Y represents a straight chain or branched chain alkyl group having from 1 to 8 carbon atoms, a trifluoromethyl group, a straight chain or branched chain alkenyl group having from 2 to 8 carbon atoms, a cycloalkyl group having from 3 to 8 carbon atoms, an alkoxy group having from 1 to 8 carbon atoms or a halogen (excepting para-substituted chlorine), m and n represent 0, 1, 2 or 3, === represents a double bond or a single bond, A is —$(D)_b$—$(CH_2)_c$— (where D is sulphur, oxygen or $NR^5$ (where $R^5$ represents hydrogen or a straight chain or branched chain alkyl group having from 1 to 8 carbon atoms), or $CH_2$, b is 0 or 1, c is 0, 1, 2, or 3), or —$(CH=CH)_d$—CH= (where d is 0 or 1, and when A represents —$(CH=CH)_d$—CH=, B is not present), B represents hydrogen, a straight chain or branched chain alkyl group having from 1 to 8 carbon atoms, a hydroxyl group or a trialkylsiloxy group (where the alkyl groups are straight chain or branched chain alkyls having from 1 to 8 carbon atoms), and $R^1$, $R^2$, $R^3$ and $R^4$ are each hydrogen, a straight chain or branched chain alkyl group having from 1 to 8 carbon atoms or a pharmacologically permitted cation, and they may be the same or different], or a hydrate thereof.

Furthermore, the present invention is an implant attachment stabilization method, a method for the inhibition of interstitial tissue proliferation and a method for the inhibition of the production of osteolytic factors, which is characterized in that there is administered an effective dose of a methane-bisphosphonic acid derivative represented by aforesaid general formula (I), or hydrate thereof.

Moreover, the present invention comprises the use of a methanebisphosphonic acid derivative represented by aforesaid general formula (I), or hydrate thereof, for the production of an implant attachment stabilizer, an interstitial tissue proliferation inhibitor and an osteolytic factor production inhibitor.

The substituent groups in the methanebisphosphonic acid derivatives represented by aforesaid general formula (I) are, more specifically, as follows.

Examples of the straight chain or branched chain unsubstituted, or nitrogen, oxygen or silicon atom substituent-containing, alkyl group with from 1 to 8 carbon atoms, employed as X in the substituent group XS, are methyl, ethyl, propyl, isopropyl, butyl, isobutyl, t-butyl, pentyl, hexyl, cyclobutyl, cyclopentyl, cyclohexyl, cyclopentylmethyl, cyclohexylmethyl, 2-aminoethyl, 2-N-methylaminoethyl, 2-N,N-dimethylaminoethyl, 2-hydroxyethyl, 2-alkoxyethyl, 2-trialkylsiloxyethyl, 2-aminopropyl, 2-N-methylaminopropyl, 2-N,N-dimethylaminopropyl, 3-aminopropyl, 3-N- methylaminopropyl, 3-N,N-dimethylaminopropyl, 2-hydroxypropyl, 2-alkoxypropyl, 2-trialkylsiloxypropyl and the like. Again, X may otherwise be phenyl, a substituted-phenyl, naphthyl or a substituted-naphthyl. Where the substituents on the phenyl or naphthyl group are straight chain or branched chain alkyl groups with from 1 to 8 carbon atoms, examples thereof are methyl, ethyl, propyl, isopropyl, butyl, isobutyl, t-butyl, pentyl, hexyl, cyclopentylmethyl, cyclohexylmethyl and the like, and where they are straight chain or branched chain alkoxy groups with from 1 to 8 carbon atoms, examples are methoxy, ethoxy, n-propoxy, isopropoxy, n-butoxy, pentyloxy, hexyloxy and the like. The halogen is fluorine, chlorine, bromine or iodine. The position of the XS substituent group is para-, meta- or ortho-.

Where substituent group Y is a straight chain or branched chain alkyl group with from 1 to 8 carbon atoms, examples are methyl, ethyl, propyl, isopropyl, butyl, isobutyl, t-butyl, pentyl, hexyl, cyclopentylmethyl, cyclohexylmethyl and the like. Where it is a straight chain or branched chain alkenyl group with 2 to 8 carbon atoms, examples are vinyl, allyl, 1-propenyl, isopropenyl, butenyl, pentenyl and the like. Where it is a cycloalkyl group with 3 to 8 carbon atoms, examples are cyclopropyl, cyclobutyl, cyclopentyl, cyclohexyl and the like. Where it is an alkoxy group with from 1 to 8 carbon atoms, examples are methoxy, ethoxy, n-propoxy, isopropoxy, n-butoxy, pentyloxy, hexyloxy and the like. Where it is a halogen, examples are fluorine, chlorine (excluding the case of chlorine substituted in the para-position), bromine and iodine. There are no particular restrictions on the position of substituent group Y.

In the case where A is $—(D)_b—(CH_2)_c—$ and === denotes a single bond, D is sulphur, oxygen, $NR^5$ ($R^5$ represents hydrogen or a straight chain or branched chain alkyl group with 1 to 8 carbon atoms) or $CH_2$, b is 0 or 1, and c is 0, 1, 2 or 3 (but in the case where b=0, then c=0). More preferably, b and c are independently 0 or 1.

Furthermore, where B is a hydroxyl group or a trialkylsiloxy group (where the alkyl groups are straight chain or branched chain alkyls with 1 to 8 carbon atoms) and, furthermore, D is sulphur, oxygen or $NR^5$ ($R^5$ is as defined above) and b=1, the compounds where c=0 are chemically unstable, so are undesirable. However, in the case where c is 1, 2 or 3, they are stable and are desirable compounds. Specific examples of particularly preferred cases of A are S, NH, O, $CH_2$, $CH_2CH_2$, $SCH_2$, $SCH_2CH_2$, $SCH_2CH_2CH_2$, $NHCH_2$, $OCH_2$ and the like. Furthermore, also included are those compounds where there is no interposed A (that is to say, the case where the phenyl group is directly connected to the carbon of the bisphosphonic acid. Again, the case where A is $—(CH=CH)_d—CH=$, means that === denotes a double bond and no B is present, and here d is 0 or 1.

Examples of the straight chain or branched chain alkyl groups with 1 to 8 carbon atoms denoted by B, $R^1$, $R^2$, $R^3$, $R^4$ and $R^5$ are methyl, ethyl, propyl, isopropyl, butyl, isobutyl, t-butyl, pentyl, hexyl, cyclopentylmethyl, cyclohexylmethyl and the like. Furthermore, the same examples can be given for the straight chain or branched chain alkyls with 1 to 8 carbon atoms in the case where B is a trialkylsiloxy group (in which the alkyl groups are straight chain or branched chain alkyls with 1 to 8 carbon atoms).

The pharmacologically permitted cations represented by $R^1$, $R^2$, $R^3$ and $R^4$ are metal cations or ammonium $NR_4$ (where R is hydrogen or a straight chain or branched chain alkyl group with 1 to 8 carbon atoms). Particularly preferred metal cations are the cations of alkali metals such as lithium, sodium and potassium, and of alkaline earth metals such as magnesium and calcium. However, the cations of other metals such as aluminium, zinc, iron and the like are also included in the present invention. Ammonium refers to ammonium based on ammonia, primary amines, secondary amines and tertiary amines, and also quaternary ammonium. Examples thereof are ammonia, methylamine, dimethylamine, trimethylamine, ethylamine, diethylamine, triethylamine, propylamine, dipropylamine, isopropylamine, diisopropylamine, butylamine, dibutylamine, isobutylamine, t-butylamine, monoethanolamine, diethanolamine and triethanolamine, and also tetramethylammonium, tetraethylammonium and the like. Of these, the cations of sodium, potassium, ammonia and alkylamines are preferred.

The cations represented by $R^1$ to $R^4$ may be the same or different, and again included in the invention are mixtures of cations and hydrogen such as, for example, a monocationic salt, bicationic salt, tricationic salt or tetracationic salt. Preferably, the methane-bisphosphonic acid derivative represented by general formula (I) is one where $R^1$ to $R^4$ are all hydrogen, one where three of $R^1$ to $R^4$ are hydrogen and the remaining one is sodium or where three are hydrogen and the remaining one is ammonium, or where two of $R^1$ to $R^4$ are hydrogen and the remaining two are sodium or two are hydrogen and the remaining two are ammonium.

Among the methanebisphosphonic acid derivatives represented by general formula (I), the compounds where X is a straight chain or branched chain alkyl group with from 1 to 8 carbon atoms, Y is a straight chain or branched chain alkyl group with from 1 to 8 carbon atoms, a trifluoromethyl group, a straight chain or branched chain alkenyl group with from 2 to 8 carbon atoms, a cycloalkyl group with 3 to 8 carbon atoms, an alkoxy group with 1 to 8 carbon atoms or a halogen (excluding the case of chlorine substituted in the para-position), m and n are 0 or 1, === is a single bond, A is $—S—(CH_2)_c—$ (c is 1, 2 or 3), B is hydrogen or a straight chain or branched chain alkyl group with from 1 to 8 carbon atoms, $R^1$, $R^2$, $R^3$ and $R^4$ are each hydrogen, a straight chain or branched chain alkyl group with from 1 to 8 carbon atoms, or a physiologically acceptable cation, and these may be the same or different, are preferred. (4-methylthiophenyl) thiomethane-1,1-bis-phosphonic acid is further preferred.

The methanebisphosphonic acid derivatives represented by general formula (I) can be produced by the method disclosed in JP-B-8–26048.

The methanebisphosphonic acid derivatives represented by general formula (I) and the hydrates thereof have an interstitial tissue proliferation inhibiting action and an osteolytic factor production inhibiting action. In particular, they have actions such as inhibiting the proliferation of interstitial tissue like granulation tissue at the implant periphery and inhibiting the production of osteolytic factors at the implant periphery, and they have the effect that the period of implant attachment is prolonged. As osteolytic factors, the production of which is to be inhibited, there are cytokines, examples of which are interleukin-1, interleukin-6 and TNFα.

Thus, the compounds relating to the present invention are useful as interstitial tissue proliferation inhibitors or osteolytic factor production inhibitors and, in particular, they are valuable in the prevention of implant loosening or detachment after implant attachment. Here, implant denotes an artificial joint, artificial bone or biologically-derived tissue used in the field of orthopaedic surgery, or an artificial or biologically-derived oro-dental prosthetic material used in the oro-dental field.

In the case where a compound of the present invention is used as an implant attachment stabilizer, interstitial tissue proliferation inhibitor or osteolytic factor production inhibitor, it can be offered for use either as it is or as a medical composition mixed with known pharmacologically-permitted supports, fillers and the like. Administration may be by oral administration as tablets, capsules, powders, granules, pills or the like, or by parenteral administration such as by means of injection, ointment or suppository, or by administration around the implant at the time of the implant attachment using a suitable retaining agent as a support. The amount administered will differ with the subject, administration route and the symptoms but will be from about 0.1 mg to about 5 g, and preferably from about 1 mg to about 2 g, and this dose can be subdivided and administered orally or parenterally a number of times per day or once per period ranging from 1 to 7 days.

Below, the present invention is explained in still more specific terms by providing examples.

EXAMPLE 1

Inhibition of Granulation Tissue Formation in a Rat Osteolysis Model

The following pharmacological test was carried out using as the test drug, (4-methylthiophenyl)thiomethane-1,1-bisphosphonic acid disodium salt (hereinafter referred to as Compound 1). From the central part of a distal femur of 10 week old female Wistar rats, Kirschner wire (made of stainless steel) was fixed in the bone marrow. The osteolysis model was then prepared by attaching an osmotic pump, in which had been introduced 200 µl of rat serum containing 0.1 mg of 2–3 mm diameter polyethylene particles, beneath the skin of the back of the rat and continuously infusing polyethylene particles from the osmotic pump into the knee joint cavity.

Compound 1 was dissolved in sterile distilled water as a solvent and, in the proportion of 1 ml per 1 kg body weight (1 mg/kg), this was administered subcutaneously, 3 times a week from the day after preparation of the osteolysis model. Four weeks after preparation of the osteolysis model, the femur was collected.

After removing the Kirschner wire, the collected femur was fixed in formalin buffer solution and then decalcified. Next, the femur was embedded in paraffin and a frontal plane tissue section prepared. A histopathological specimen was prepared by subjecting the tissue section to haematoxylin/eosin (HE) staining.

In order to examine the formation of granulation tissue histomorphometrically, the prepared histopathological specimen was projected onto a computer image analyzer tablet and the area of granulation tissue which had formed at the periphery of the Kirschner wire was measured. Furthermore, by measuring the length of the surface of the Kirschner wire in contact with the bone marrow (the surrounded length of the Kirschner wire) and dividing the granulation tissue area by the surrounded length of the Kirschner wire, an index of granulation tissue formation (a proliferation index) was obtained.

The results of measurements of representative examples of the compound non-administration and Compound 1 administration animals are shown in Table 1.

TABLE 1

Histomorphometrical findings for the rat osteolysis model - granulation tissue proliferation index- (4th week after treatment)

|  | Granulation cell proliferation index ($\mu m^2$/mm) |
|---|---|
| Non-administration animal | 1017.02 |
| Compound 1 administration animal | 93.05 |

As is clear from Table 1, Compound 1 inhibited the formation of granulation cells occurring 4 weeks after the preparation of the osteolysis model.

EXAMPLE 2

Inhibition of Interleukin-1α (IL-1α) Production Within Granulation Tissue in the Rat Osteolysis Model In an osteolysis model prepared in the same way as in Example 1, granulation tissue was collected either 4 weeks or 8 weeks after the model preparation. Compound 1 was administered in the same way as in Example 1. Isogen was added in the proportion of 1 ml to 100 mg of granulation tissue and, after cutting finely using scissors, homogenisation was performed. To this was added 0.2 ml of chloroform, after which the aqueous phase was recovered. To this aqueous phase, 0.5 ml of isopropanol was then added and, after leaving to stand at room temperature for 10 minutes, centrifuging was carried out. To the sediment, 1 ml of 75% ethanol was added and centrifuging performed, then the sediment obtained dried by vacuum centrifugation, after which 20 µl of SDS was added to give an RNA sample. This sample was subjected to the RT-PCR method and IL-1α production measured. The sample subjected to the RT-PCR method was subjected to electrophoresis and the IL-1α band and, for correction purposes, a β-actin band in the same sample, were determined quantitatively using a computer image analyzer and the resultant ratio of IL-1α expression to β-actin expression (IL-1α band/β-actin band×100) was used as an index. The results of measurements of representative examples of the compound non-administration and Compound 1 administration animals are shown in Table 2.

Table 2

IL-1α Production in Granulation Tissue in the Rat Osteolysis Model

|  | 4th week after treatment (IL-1α/β-actin × 100) | 8th week after treatment (IL-1α/β-actin × 100) |
|---|---|---|
| Non-administration animal | 66.7 | 117.5 |
| Compound 1 administration animal | 33.7 | 16.1 |

As is clear from Table 2, Compound 1 inhibited the production of IL-1α in granulation tissue 4 weeks and 8 weeks after preparation of the osteolysis model.

EXAMPLE 3

Inhibition of TNFα Production in Granulation Tissue in the Rat Osteolysis Model In an osteolysis model prepared in the same way as in Example 1, granulation tissue was collected 4 weeks or 8 weeks after the model preparation. Compound 1 was administered in the same way as in Example 1. Isogen was added in the proportion of 1 ml to 100 mg of granulation tissue and, after cutting finely using scissors, homogenisation was performed. To this was added 0.2 ml of chloroform, after which the aqueous phase was recovered. To this aqueous phase, 0.5 ml of isopropanol was then added and, after leaving to stand at room temperature for 10 minutes, centrifuging was carried out. To the sediment, 1 ml of 75% ethanol was added and centrifuging performed, then the sediment obtained dried by vacuum centrifugation, after which 20 μl of SDS was added to give an RNA sample. This sample was subjected to the RT-PCR method and TNFα production measured.

The sample subjected to the RT-PCR method was subjected to electrophoresis and the TNFα band and, for correction purposes, a β-actin band in the same sample, were determined quantitatively using a computer image analyzer and the resultant ratio of TNFα expression to β-actin expression (TNFα band/β-actin band×100) was used as an index. The results of measurements of representative examples of the compound non-administration and Compound 1 administration animals are shown in Table 3.

TABLE 3

TNFα production in granulation tissue in the rat osteolysis model

| | 4th week after treatment (TNFα/β-actin × 100) | 8th week after treatment (TNFα/β-actin × 100) |
|---|---|---|
| Non-administration animal | 5.0 | 31.2 |
| Compound 1 administration animal | 1.0 | 0.4 |

As is clear from Table 3, Compound 1 inhibited the production of TNFα in granulation tissue 4 weeks and 8 weeks after preparation of the osteolysis model.

EXAMPLE 4

Inhibition of Osteolysis in the Rat Osteolysis Model

In an osteolysis model prepared in the same way as in Example 1, femurs were collected 4 weeks or 8 weeks after the model preparation. Compound 1 was administered in the same way as in Example 1.

The collected femurs were subjected to soft X-ray imaging in the state with the Kirschner wire inserted. It was found as a result that, 4 weeks and 8 weeks after the osteolysis model preparation, in the non-administration group the bone density at the Kirschner wire periphery was low and osteolysis had occurred, but in the case of the Compound 1 administration group osteolysis had been inhibited.

EXAMPLE 5

Inhibition of Bone Resorption Marker Elimination in the Rat Osteolysis Model In order to test biochemically the degree of bone resorption, using deoxypyridinoline elimination in the urine as an index, preparation of an osteolysis model was carried out in the same way as in Example 1.

Compound 1 was administered in the same way as in Example 1. Twenty-four hour pooled urine was collected 4 weeks and 8 weeks after preparation of the osteolysis model, and the deoxypyridinoline concentration in the urine measured using an ELISA method. The value obtained, divided by the creatinine concentration in the urine, was taken as the measurement result.

The measurement results obtained are shown in Table 4 as the mean values±standard errors. Also, in the table, the result of a statistical analysis by the Student's T test (comparing with the non-administration group) is indicated by ** (significance level P<0.01).

TABLE 4

Bone resorption marker changes in the rat osteolysis model - deoxypyridinoline in urine - (mean value ± standard deviation)

| | 4th week after treatment (nM/mM creatinine | 8th week after treatment (nM/mM creatinine) |
|---|---|---|
| Non-administration animals | 66.45 ± 4.30 (n = 7) | 43.26 ± 4.16 (n = 9) |
| Compound 1 administration animals | 55.53 ± 8.15 (n = 8) | 28.30 ± 2.43** (n = 10) |

**P < 0.01 vs non-administration group

As is clear from Table 4, Compound 1 significantly inhibited the deoxypyridinoline elimination in the urine 8 weeks after preparation of the osteolysis model.

INDUSTRIAL APPLICATION POTENTIAL

The methanebisphosphonic acid derivatives of the present invention, which are represented by general formula (I), and hydrates thereof, have an interstitial tissue proliferation inhibiting action or an osteolysis factor production inhibiting action. In particular, since they inhibit osteolysis as a result of their actions in inhibiting the interstitial tissue proliferation accompanying implant attachment and in inhibiting osteolysis factor production at the implant periphery, they are useful as attachment stabilizers for implants such as artificial joints and for implants in the oro-dental field.

What is claimed is:

1. A method of stabilizing an implant comprising administering orally, parenterally or externally an effective amount of a methanebisphosphonic acid derivative represented by formula (I)

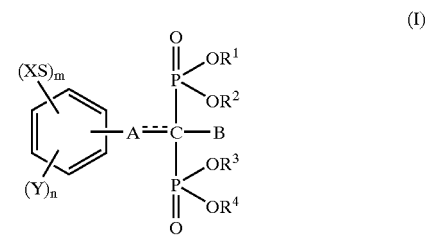

(I)

where, in the formula, X represents a straight chain or branched chain unsubstituted, or nitrogen, oxygen or silicon atom substituent-containing, alkyl group with from 1 to 8 carbon atoms, a phenyl group or a naphthyl group, or a phenyl or naphthyl group substituted with a straight chain or branched chain alkyl group having from 1 to 8 carbon atoms, a straight chain or branched chain alkoxy group having from 1 to 8 carbon atoms, a halogen or a hydroxyl group, Y represents a straight chain or branched chain alkyl group having from 1 to 8 carbon atoms, a trifluoromethyl group, a straight chain or branched chain alkenyl group having from 2 to 8 carbon atoms, a cycloalkyl group having from 3 to 8 carbon atoms, an alkoxy group having from 1 to 8 carbon atoms or a halogen, excluding para-substituted chlorine, m represents 1, 2 or 3 and n represents 0 1, 2 or 3, ══ represents a single bond, A is —$(D)_b$—$(CH_2)_c$— where D is sulfur, b is 1, c is 0, 1, 2, or 3 B represents hydrogen, a straight chain or branched chain alkyl group having from 1 to 8 carbon atoms, a hydroxyl group or a trialkylsiloxy group where the alkyl groups are straight chain or branched chain alkyls having from 1 to 8 carbon atoms, and $R^1$, $R^2$, $R^3$ and $R^4$ are independently hydrogen, a straight chain or branched chain alkyl group having from 1 to 8 carbon atoms or a pharmacologically acceptable cation, or hydrate thereof.

2. A method according to claim 1 where, in formula (I), X is a straight chain or branched chain alkyl group with 1 to 8 carbon atoms, m is 1 and n is 0 or 1, ══ is a single bond, A is —S—$(CH_2)_c$— (where c is as defined in claim 1), B is hydrogen or a straight chain or branched chain alkyl group with 1 to 8 carbon atoms and $R^1$, $R^2$, $R^3$ and $R^4$ are as defined in claim 1.

3. A method for inhibiting interstitial tissue proliferation comprising orally, parenterally or externally administering an effective amount of a methanebisphosphonic acid derivative represented by formula (I)

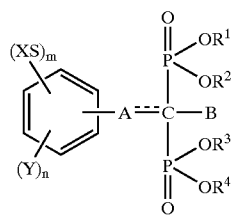

(I)

where, in the formula, X represents a straight chain or branched chain unsubstituted, or nitrogen, oxygen or silicon atom substituent-containing, alkyl group with from 1 to 8 carbon atoms, a phenyl group or a naphthyl group, or a phenyl or naphthyl group substituted with a straight chain or branched chain alkyl group having from 1 to 8 carbon atoms, a straight chain or branched chain alkoxy group having from 1 to 8 carbon atoms, a halogen or a hydroxyl group, Y represents a straight chain or branched chain alkyl group having from 1 to 8 carbon atoms, a trifluoromethyl group, a straight chain or branched chain alkenyl group having from 2 to 8 carbon atoms, a cycloalkyl group having from 3 to 8 carbon atoms, an alkoxy group having from 1 to 8 carbon atoms or a halogen, excluding para-substituted chlorine, m represents 1,2 or 3 and n represents 0, 1, 2 or 3, ══ represents a single bond, A is —$(D)_b$—$(CH_2)_c$— where D is sulfur, b is 1, c is 0, 1, 2, or 3 B represents hydrogen, a straight chain or branched chain alkyl group having from 1 to 8 carbon atoms, a hydroxyl group or a trialkylsiloxy group where the alkyl groups are straight chain or branched chain alkyls having from 1 to 8 carbon atoms, and $R^1$, $R^2$, $R^3$ and $R^4$ are independently hydrogen, a straight chain or branched chain alkyl group having from 1 to 8 carbon atoms or a pharmacologically acceptable cation, or hydrate thereof.

4. A method according to claim 3 where, in formula (I), X is a straight chain or branched chain alkyl group with 1 to 8 carbon atoms, m is 1 and n is 0 or 1, ══ is a single bond, A is —S—$(CH_2)_c$— (where c is as defined in claim 3, B is hydrogen or a straight chain or branched chain alkyl group with 1 to 8 carbon atoms and $R^1$, $R^2$, $R^3$ and $R^4$ are as defined in claim 3.

5. A method according to claim 1 where the implant is an artificial joint, artificial bone, biologically-derived tissue, or an artificial or biologically-derived oro-dental prosthetic material used in the oro-dental field.

6. A method according to claim 1 where the implant is a dental material.

* * * * *